United States Patent
Schuerch

Patent Number: 6,012,456
Date of Patent: Jan. 11, 2000

[54] ARTHROSCOPIC LEG HOLDER

[76] Inventor: Peter Schuerch, 42 Bayview Ave., Quincy, Mass. 02169

[21] Appl. No.: 09/024,010

[22] Filed: Feb. 14, 1998

Related U.S. Application Data

[60] Provisional application No. 60/037,934, Feb. 14, 1997.
[51] Int. Cl.$^7$ .................................................. A61B 19/00
[52] U.S. Cl. ........................................... 128/869; 128/882
[58] Field of Search .................................... 128/845, 846, 128/869, 882; 606/237; 602/36–41; 5/600; 269/328

[56] References Cited

U.S. PATENT DOCUMENTS

| | | | |
|---|---|---|---|
| 988,923 | 4/1911 | Bauerfeind | 269/328 |
| 4,299,213 | 11/1981 | Violet | 128/882 |
| 4,373,709 | 2/1983 | Whitt | 128/882 |
| 4,457,302 | 7/1984 | Caspari | 128/882 |

*Primary Examiner*—Michael A. Brown
*Attorney, Agent, or Firm*—John M. Brandt

[57] ABSTRACT

A holder for positioning and immobilizing a leg for surgical procedures on an operating table having a pair of opposed curved leg holding members each mounted on a base slidably and rotatably mounted on a rod adapted to be horizontally mounted in relation to the table. Each base and leg holder is secured in a desired position by a clamp mechanism and the device includes a length of flexible cushioned tubing which fits over and between the leg holding members to provide a unified leg support surface.

3 Claims, 2 Drawing Sheets

ARTHROSCOPIC LEG HOLDER

CROSS REFERENCE TO RELATED APPLICATION

This application is a formal application based on a disclosure submitted as a provisional application entitled Arthroscopic Leg Holder Ser. No. 60/037,934 filed Feb. 14, 1997 by the same inventor.

BACKGROUND OF THE INVENTION

1. Field of the Invention

The invention resides in the field of supports used to position and hold patient limbs during surgical procedures and more specifically relates to a device for securing a leg in a selected raised position.

2. Description of the Prior Art

The inventor is aware of two devices designed for the same purpose of securing a leg. The first manufactured by Orthopedic Systems, Inc. of San Jose, Calif. utilizes two opposed holding members arranged to encircle the leg, one fixed to a horizontal support which in turn is attached to a vertical rod arranged to be slidably clamped to the side of an operating table; the other member slidably mounted in the vertical direction mounted on the same horizontal support.

The second manufactured by O. R. Direct of Acton, Mass. consists of two opposed leg holding members also intended to encircle the leg which slide on a horizontal bar and pivot apart in the same plane. The horizontal bar is similarly arranged to be slidably clamped to the side of an operating table.

In contrast to the prior art, applicant's invention supplies an additional dimension of positional adjustment by allowing each leg holding member to rotate about as well as slide along a horizontal support bar. The combination further includes a length of flexible tubing which fits over and bridges both supports to provide a unitary cushion regardless of the position of the leg holding members.

SUMMARY OF THE INVENTION

The invention may be summarized as an arthroscopic leg holder comprising two opposed spaced apart inwardly curving leg holding members each mounted on a base each of which bases is in turn slidably and rotatably mounted on a horizontal bar.

The horizontal bar is adapted to be clamped to an operating table in a horizontal position by, for example, a vertical rod attached thereto. A length of flexible tubing comprised of, for example, foam rubber fits over and bridges the two leg holders providing a cushioned base upon which the leg rests.

Each base is clamped in a desired position on the horizontal bar by an individual clamp, for example, a lever actuated cam operated quick release device of the well known type used to secure bicycle wheels to bicycle frames.

The leg holders are therefore free to slide and rotate within the confines of the flexibility of the cushioning tube which, as will be illustrated below, greatly facilitates the setting up of a leg for a surgical procedure.

These and other features and advantages of the invention will become more clear from the drawings and description of the preferred embodiment which follows.

DESCRIPTION OF THE PREFERRED EMBODIMENT

Figure 1:
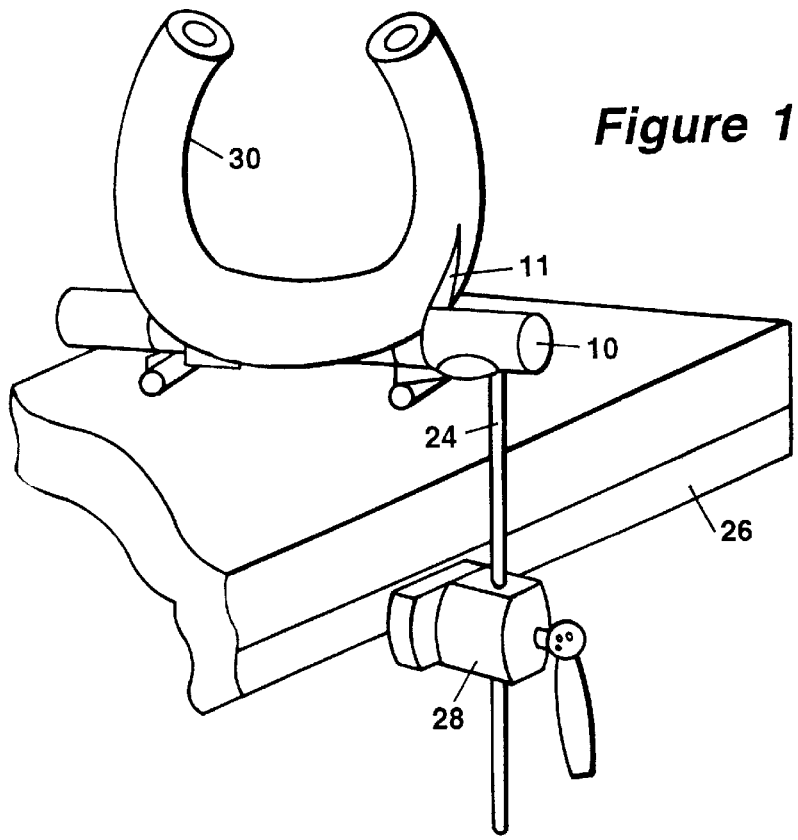
FIG. 1 is a perspective illustration of the preferred embodiment of the invention.

Referring first to FIG. 1, there is showing a perspective view of the preferred embodiment of the invention in which horizontal bar 10 has mounted thereon leg holding member bases 12 and 14 secured by clamp members 16 and 18. Leg holding members 20 and 22 are attached to bases 12 and 14 respectively. Bar 10 is attached to vertical bar 24 which serves to mount the entire device on operating table 26 by clamp 28. Flexible tubing 30 comprised of, for example, foam rubber entirely covers leg holding members 20 and 22 through the expedient of a slot in the middle bottom extending approximately one third the length of the cover.

Figure 3:
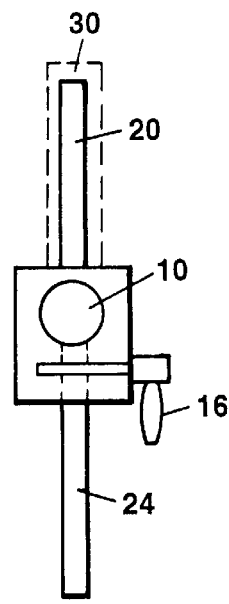
FIG. 3 is an end view of the embodiment of FIG. 1.
Figure 2:
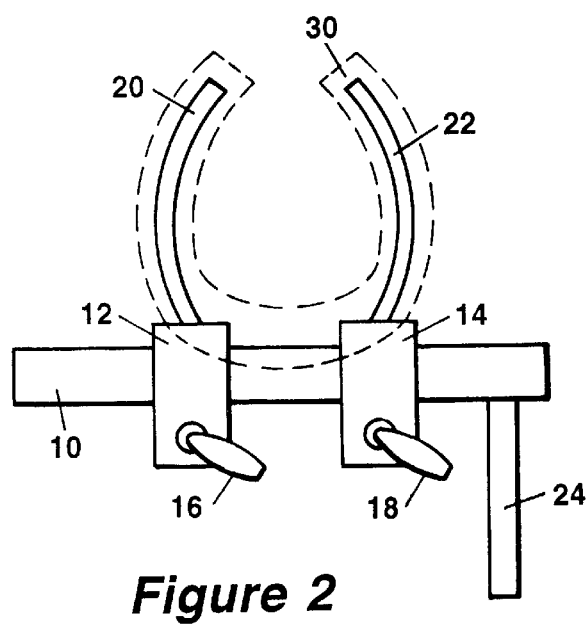
FIG. 2 is a side view of the embodiment of FIG. 1.

FIGS. 2 and 3 illustrate side and end views of preferred embodiment of FIG. 1 with tubing 30 shown in dashed format wherein like numbers refer to like parts. The leg holding members, their bases and the horizontal bar are all composed of surgical grade stainless steel. The clamps as mentioned above are well known lever actuated cam operated quick release bicycle style devices. As will be seen, flexible tubing 30 is designed to be removed and replaced after each use for sanitary purposes.

Figure 4C:
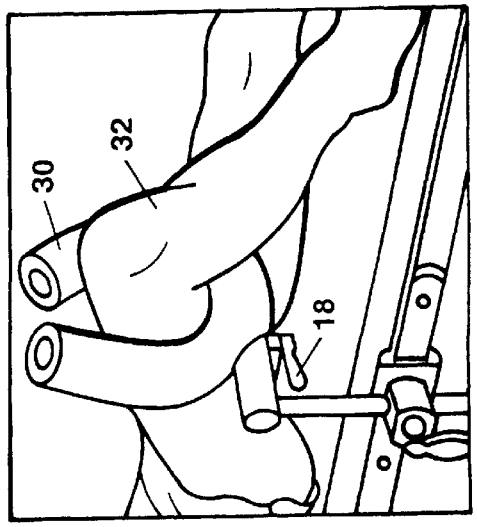
FIGS. 4a, 4b, and 4c are illustrations of the preferred embodiment in use.
Figure 4B:
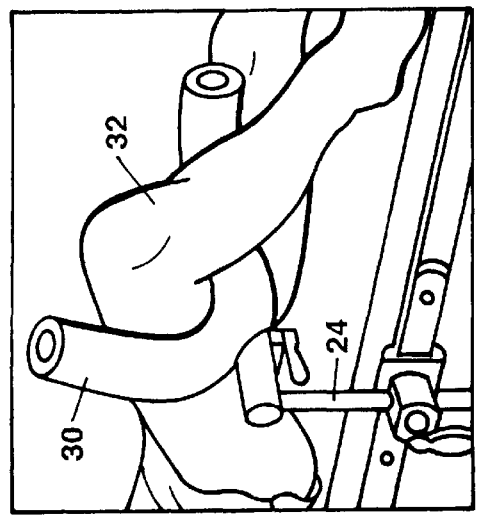
Figure 4A:
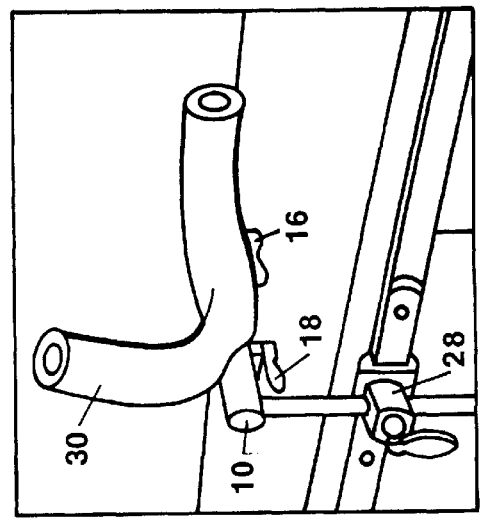

Referring to FIGS. 4a, b, and c, the use of the invention is illustrated. In FIG. 4a, one base and leg holder is rotated downward after release of the appropriate clamp. The advantageous flexibility of tube 30 is shown and in FIG. 4b wherein patient leg 32 has been placed between the two leg holding members FIG. 4c illustrates the previously rotated leg holder returned to its original position and slid inwardly toward the opposite leg holder and clamped in place to complete the procedure. As variations in the above described embodiment will now become apparent to those skilled in the art, the invention is accordingly defined by the following claims.

What is claimed is:

1. An Arthroscopic leg holder for surgical procedures on an operating table comprising in combination:

a. a bar adapted to be mounted horizontally with respect to said table;

b. first and second base members each independently rotatably and slidably mounted on said bar;

c. first and second clamp means one each associated with each of said base members to secure each base in a selected position on said bar;

d. first and second curved leg holding members in opposed concave relationship one each mounted on each base; and e. a length of partially slotted flexible tubing adapted to fit over and conform between said leg holding members to provide thereby a unified leg support surface.

2. The apparatus of claim 1 wherein said clamps comprise lever actuated cam operated bicycle wheel clamps.

3. The apparatus of claim 1 wherein said flexible tubing comprises foam rubber.

* * * * *